(12) United States Patent
Novell

(10) Patent No.: US 11,172,914 B2
(45) Date of Patent: Nov. 16, 2021

(54) LAPAROSCOPIC FLEXIBLE SUCTION DEVICE AND ASSOCIATED METHODOLOGY

(71) Applicant: Fifth Arm Surgical, LLC, Cheyenne, WY (US)

(72) Inventor: Robert F. Novell, Colorado Springs, CO (US)

(73) Assignee: FIFTH ARM SURGICAL, LLC, Cheyenne, WY (US)

( * ) Notice: Subject to any disclaimer, the term of this patent is extended or adjusted under 35 U.S.C. 154(b) by 326 days.

(21) Appl. No.: 16/388,244

(22) Filed: Apr. 18, 2019

(65) Prior Publication Data

US 2019/0321019 A1   Oct. 24, 2019

Related U.S. Application Data

(60) Provisional application No. 62/659,821, filed on Apr. 19, 2018.

(51) Int. Cl.
*A61B 17/00* (2006.01)
*A61M 1/00* (2006.01)
(Continued)

(52) U.S. Cl.
CPC .... *A61B 17/00234* (2013.01); *A61B 1/00094* (2013.01); *A61B 1/015* (2013.01);
(Continued)

(58) Field of Classification Search
CPC .............. A61M 1/0023; A61M 1/0058; A61M 2205/0266; A61M 25/0041; A61M 25/007; A61M 25/008; A61M 25/0102; A61B 2217/007; A61B 2217/005; A61B 2017/00867; A61B 2017/00862;
(Continued)

(56) References Cited

U.S. PATENT DOCUMENTS 3,426,759 A * 2/1969 Smith .................. A61M 1/008
604/264
4,487,600 A    12/1984 Brownlie et al.
(Continued)

FOREIGN PATENT DOCUMENTS

WO    2009/131912 A1    10/2009
WO    2017/040711 A1    3/2017

OTHER PUBLICATIONS

Patent Cooperation Treaty, "International Search Report and Written Opinion"; PCT International Application No. PCT/US2019/055373; dated Jan. 3, 2020 (Jan. 3, 2020).
(Continued)

*Primary Examiner* — Deanna K Hall
(74) *Attorney, Agent, or Firm* — Martensen IP; Michael C. Martensen

(57) ABSTRACT

A laparoscopic flexible suction/irrigation device of the present invention encases a inner rigid cannula with an outer flexible cannula. Upon translating the distal end of outer flexible cannula beyond the distal end of the inner rigid cannula, the outer flexible cannula returns to a preexisting curvilinear shape. This curved extension can thereafter be positioned via a proximal handle to concavities within the surgical site for precise and effective fluid retraction.

18 Claims, 8 Drawing Sheets

(51) Int. Cl.
 *A61B 1/00* (2006.01)
 *A61B 1/015* (2006.01)

(52) U.S. Cl.
 CPC ........ *A61M 1/0023* (2013.01); *A61M 1/0058* (2013.01); *A61M 1/85* (2021.05); *A61B 2017/003* (2013.01)

(58) Field of Classification Search
 CPC ........... A61B 2017/00336; A61B 2017/00331; A61B 1/015
 See application file for complete search history.

(56) References Cited

U.S. PATENT DOCUMENTS

| | | |
|---|---|---|
| 4,767,404 A | 8/1988 | Renton |
| 5,295,956 A | 3/1994 | Bales et al. |
| 5,505,710 A | 4/1996 | Dorsey, III |
| 5,814,058 A | 9/1998 | Carlson et al. |
| 6,168,577 B1 | 1/2001 | Niederjohn et al. |
| 6,447,523 B1 | 9/2002 | Middleman et al. |
| 7,025,755 B2 | 4/2006 | Epstein |
| 8,657,840 B2 | 2/2014 | Palmer et al. |
| 2005/0043682 A1* | 2/2005 | Kucklick ............ A61M 3/0279 604/164.09 |
| 2005/0107860 A1 | 5/2005 | Ignagni et al. |
| 2010/0010524 A1 | 1/2010 | Barrington et al. |
| 2013/0164706 A1 | 6/2013 | Odabashian et al. |
| 2015/0119851 A1 | 4/2015 | Hoogenakker et al. |
| 2016/0038660 A1 | 2/2016 | Loebl |
| 2017/0056571 A1 | 3/2017 | Santanello |

OTHER PUBLICATIONS

Santanello Surgical, LLC, (https://www.vampirosuction.com/vampiro), Product Info Sheet, "The Vampiro" found at "https://docs.wixstatic.com/ugd/c29358_d53481044c4846a79aa958eb5e7dbaba.pdf", Columbus, OH 43221 (updated Feb. 2018).

* cited by examiner

LAPAROSCOPIC FLEXIBLE SUCTION DEVICE AND ASSOCIATED METHODOLOGY

RELATED APPLICATION

The present application relates to and claims the benefit of priority to U.S. Provisional Patent Application No. 62/659,821 filed 19 Apr. 2018 which is hereby incorporated by reference in its entirety for all purposes as if fully set forth herein.

BACKGROUND OF THE INVENTION

Field of the Invention

Embodiments of the present invention relate, in general, to surgical devices and more particularly to a suction device used in laparoscopy procedures.

Relevant Background

Laparoscopic surgery is minimally invasive surgery, sometimes referred to as keyhole surgery, in which operations are performed through small incisions elsewhere on the body. During laparoscopic surgery a long fiber optic cable system allows viewing of the affected area (surgical site) by positioning the cable from a more distant, but easily accessed location. Laparoscopic surgery results in reduced pain and hemorrhaging due to the smaller incisions and recovery time is shorter.

There are multiple different types of laparoscopic surgery but in each case the surgeon ability to view the area being treated must remain clear of fluid and debris. To facilitate the treatment area saline solution may be introduced into the region and then removed via suction.

Many surgical instruments use suction, for example, to remove material such as tissue and fluids from the operating site. Many surgical instruments that are used to shave, cut, resect, abrade and/or remove tissue, bone and/or other bodily materials are well known and include a suction capability. Such surgical instruments can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube by which debris can be removed.

Suction devices of this type typically consist of straight rigid tubes inserted into the treatment area to introduce or remove fluid. Concavities of the surgery site however capture fluid leaving pockets or areas of fluid not readily accessible by a straight tube. These pockets of fluid have to be removed, often times via sponges which, in turn, must themselves be removed. A need therefore exists to introduce a flexible and steerable suction device that can maneuver within a surgical treatment site to introduce and remove fluid to aid in the viewing of and treatment of the surgical site. These and other deficiencies of the prior art are addressed by one or more embodiments of the present invention.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY OF THE INVENTION

The laparoscopic flexible suction/irrigation device of the present invention encases a inner rigid cannula with an outer flexible cannula. Upon translating the distal end of outer flexible cannula beyond the distal end of the inner rigid cannula the outer flexible cannula returns to a preexisting curvilinear shape. This curved extension can thereafter be positioned via a proximal handle to concavities within the surgical site for precise and effective fluid retraction.

One embodiment of the flexible suction/irrigation device of the present invention includes an elongated substantially inner rigid cannula having a first passageway (lumen) that extends from its distal end to its proximal end. A handle is connected to the proximal end of the inner rigid cannula to aid in its placement and manipulation. The invention further includes a outer flexible cannula that has a second passageway (lumen) extending therethrough. At least a portion of the inner rigid cannula is deposed within the passageway of the outer flexible cannula. Said differently, the inner rigid cannula resides inside the lumen of the outer flexible cannula. A clearance or space exists between the interior surface of the outer flexible cannula and the outer surface of the inner rigid cannula. This space enables the outer flexible cannula to translate longitudinally and radially along/around the inner rigid cannula and to allow fluid flow therebetween. Lastly, the invention includes a clamping device operable to releasably seal the interior surface of the outer flexible cannula to the exterior surface of the inner rigid cannula proximate to the proximal end of the inner rigid cannula. Upon sealing the outer flexible cannula to the exterior surface of the inner rigid cannula, suction or similar fluidic force applied to the first passageway associated with the inner rigid cannula will be realized at the distal end of the outer flexible cannula.

Other features of the laparoscopic flexible suction/irrigation device of the present invention include a vacuum source and/or a fluid source coupled to the first passageway of the inner rigid cannula. By doing so suction or irrigation can be introduced to the surgical site via the distal end of the outer flexible cannula.

The outer flexible cannula of the laparoscopic flexible suction/irrigation device, in one embodiment, possesses a curvilinear shape memory. The outer flexible cannula, having a curvilinear shape or shape memory is elastically deformable so as to accept the inner rigid cannula as it encases the inner rigid cannula. Then, responsive to a portion of the outer flexible cannula extending beyond the distal end of the inner rigid cannula, that portion of the outer flexible returns to its original curvilinear or curved shape.

Upon release of the clamping device freeing the seal between the inner surface of the outer flexible cannula and the outer surface of the inner rigid cannula, the outer flexible cannula is freely translatable along the inner rigid cannula. According to another embodiment of the present invention, the inner cannula is substantially coextensive with the outer cannula and the outer cannula is longitudinally and radially movable with respect to the inner cannula. Moreover, the outer flexible cannula is electrically non-conductive and thereby insulates the inner rigid cannula from any unwanted or random electrical discharges.

In another embodiment of the present invention, a method for localized fluid injection or removal during laparoscopic surgery using the laparoscopic flexible suction/irrigation device includes positioning the distal end of the device proximate to a surgical site. As describe above the laparoscopic flexible suction/irrigation device of the present invention includes an elongated substantially inner rigid cannula having a first passageway or lumen extending from its distal end to its proximal end. The device further includes a outer flexible cannula having a second passageway or lumen extending therethrough. At least a portion of the inner rigid cannula is deposed within the second passageway (lumen) of the outer flexible cannula. Moreover, there is a clearance or space between an interior surface of the outer flexible cannula and an outer surface of the inner rigid cannula that is operable to allow fluid flow therebetween.

The method for localized fluid injection and removal continues by sliding (translating) the outer flexible cannula along the inner rigid cannula such that the distal end of the outer flexible cannula extends beyond the distal end of the inner rigid cannula. Responsive to the distal end of the outer flexible cannula extending beyond the distal end of the inner rigid cannula process continues by releasably sealing the interior surface of the outer flexible cannula to the exterior surface of the inner rigid cannula proximate to the proximal end of the inner rigid cannula. And to remove or irrigate fluid at the surgical site a fluid force is applied to the proximal end of the first passageway of the inner rigid cannula which is realized at the distal end of the outer flexible cannula.

When a portion of the outer flexible cannula extends beyond the distal end of the inner rigid cannula, that portion of the outer flexible returns to an original curvilinear shape. This shape is helpful in reaching difficult to reach concavities location at the surgical site. The method describe above includes restoring the portion of the flexible out cannula extending beyond the distal end of the inner rigid cannula to its preexisting curved state. Recall that while the inner rigid cannula is substantially coextensive with the outer cannula, wherein the outer flexible cannula is longitudinally and radially movable with respect to the inner rigid cannula.

While the outer flexible cannula possesses a preexisting curved shape the methodology of the present invention elastically deforms the outer flexible cannula so as to conform to the inner rigid cannula when they are coextensive. And upon applying a fluid force to the proximal end of the inner rigid cannula, the laparoscopic flexible suction/irrigation device removes fluid from the surgical site (by application of a suction force) and/or injects fluid to the surgical site (upon application of a irrigation force).

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

The aforementioned and other features and objects of the present invention and the manner of attaining them will become more apparent, and the invention itself will be best understood, by reference to the following description of one or more embodiments taken in conjunction with the accompanying drawings, wherein.

Figure 1:
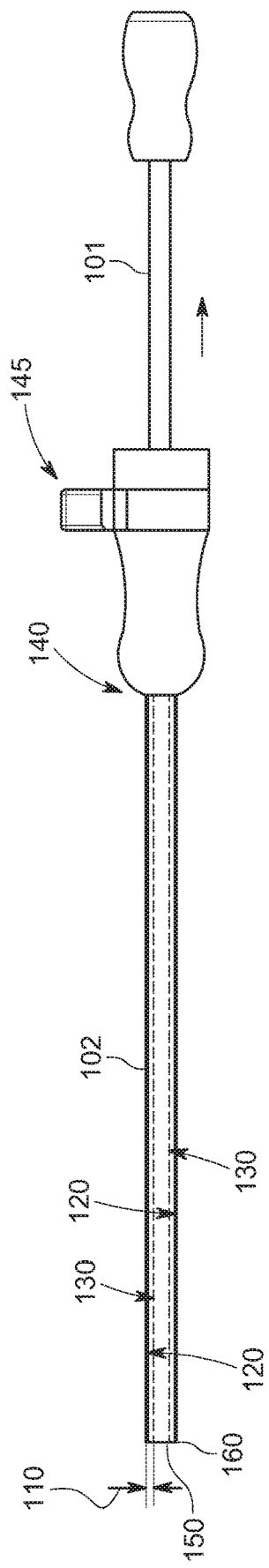
FIG. 1 shows the laparoscopic flexible suction/irrigation device, according to one embodiment of the present invention, with the outer flexible cannula retracted.

The Figures depict embodiments of the present invention for purposes of illustration only. One skilled in the art will readily recognize from the following discussion that alternative embodiments of the structures and methods illustrated herein may be employed without departing from the principles of the invention described herein.

DESCRIPTION OF THE INVENTION

A laparoscopic flexible suction/irrigation device, positional within a surgical site, provides discrete and localized fluid evacuation and irrigation. The present invention introduces a flexible curvilinear cannula into a laparoscopic surgical environment enabling surgical personnel the ability to quickly and efficiently evacuate and irrigate the surgical site. A inner rigid cannula is circumscribed by a outer flexible cannula. The combined rigid/flexible cannulas are positioned within a surgical site via a laparoscopic trocar. Once proximate to the surgical site the inner rigid cannula is partially withdrawn allowing the outer flexible cannula to return to its natural curvilinear shape. A clamp at the proximal end of the outer flexible cannula provides a fluidic seal between the inner and out cannula such that a fluid force (suction or irrigation) conveyed through the inner rigid cannula is expressed at the distal end of the outer flexible cannula.

Embodiments of the present invention are hereafter described in detail with reference to the accompanying Figures. Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The following description with reference to the accompanying drawings is provided to assist in a comprehensive understanding of exemplary embodiments of the present invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Like numbers refer to like elements throughout. In the figures, the sizes of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. Thus, for example, reference to "a component surface" includes reference to one or more of such surfaces.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be also understood that when an element is referred to as being "on," "attached" to, "connected" to, "coupled" with, "contacting", "mounted" etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Included in the description are flowcharts depicting examples of the methodology associated with the laparoscopic flexible suction/irrigation device of the present invention. It is to be understood that the blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware systems that perform the specified functions or steps, or combinations of special purpose hardware and computer instructions.

Upon reading this disclosure, those of skill in the art will appreciate still additional alternative structural and functional designs are contemplated for a laparoscopic flexible suction/irrigation device and its associated methodology through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

FIG. 1 presents one embodiment of the laparoscopic flexible suction/irrigation device of the present invention. An inner rigid cannula 101 is inserted within an outer flexible cannula 102. The outer flexible cannula 102 is dimensioned such that clearance (space) 110 exists between the interior surface 120 of the outer flexible cannula and the outer surface 130 of the inner rigid cannula. Accordingly, the outer flexible cannula 102 can freely translate along the longitude length of the inner rigid cannula 101 and allow fluid flow therebetween. The inner rigid cannula 101, which in one embodiment may comprise existing suction/hydro dissection tips includes a first passageway by which a fluidic force can be applied. The proximal end 140 of the outer flexible cannula 102 is fixedly coupled to a clamping device 145. Upon selection of a desired positional relationship between the outer and inner cannulas the clamping device 145 seals the outer flexible cannula 102 to the inner rigid cannula 101 terminating fluid flow between the interior surface 120 of the outer flexible cannula 102 and the outer surface 130 of the inner rigid cannula 101 thereby directing the fluid force to the distal end 150 of the inner rigid cannula 101 and, to the extent that the outer flexible cannula 102 is extended beyond the distal end 150 of the inner rigid cannula 102, to the distal end 160 of the outer flexible cannula 102.

As presented in FIG. 1, the distal end 160 of the outer flexible cannula 102 and the distal end 150 of the inner rigid cannula 101 are coexistent. In this configuration, upon the clamping device 145 sealing the outer flexible cannula 102 to the inner rigid cannula 101, the laparoscopic flexible suction/irrigation device of the present invention operates as a traditional laparoscopic suction/irrigation device. The laparoscopic flexible suction/irrigation device can be positioned within the surgical site to provide the surgeon with better visualization.

Figure 2:
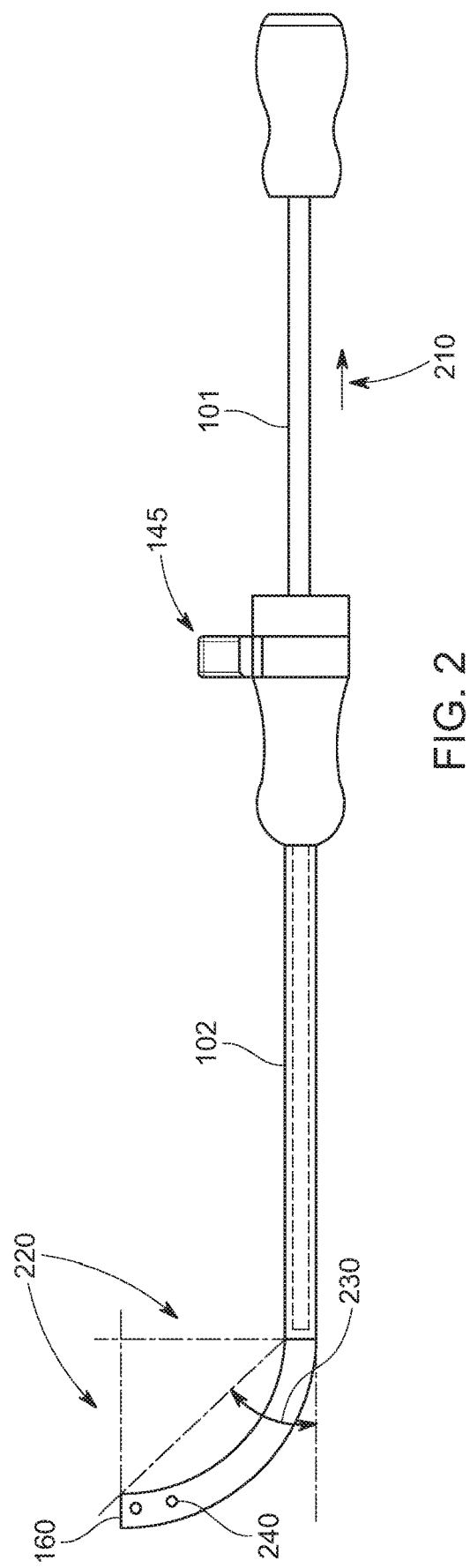
FIG. 2 shows the laparoscopic flexible suction/irrigation device, according to one embodiment of the present invention, with the outer flexible cannula extended beyond the distal end of the inner rigid cannula.

With additional reference to FIG. 2, the inner rigid cannula 101 of the laparoscopic flexible suction/irrigation device is shown to be withdrawn 210 enabling the outer flexible cannula 102 to return to its inherent or predetermined curvilinear shape 220. Upon the distal end 160 of the outer flexible cannula 102 achieving a desired degree of curvature, the clamping device 145 is once again engaged, and a fluidic force applied to the first passageway. As a seal now exists between the inner surface 120 of the outer flexible cannula 102 and the outer surface 130 of the inner cannula 101, the fluid force is conveyed to the distal end of the second passageway associated with the outer flexible cannula 102. The curved distal end 160 of the outer flexible cannula 102 enables the surgical staff to position the laparoscopic flexible suction/irrigation device around anatomical structures and into concave areas. The distal end 160 can also deconflict with other robotic instrumentation at the working site and aid in providing visualization and a cohesive working environment. Rather than moving the standard laparoscopic instruments to allow a rigid suction/irrigation device into the surgical site, the present invention can place the distal end 160 of the outer flexible cannula 102 at the needed remote area to evacuate/irrigate the site. Such flexibility and concurrent use of the laparoscopic flexible suction/irrigation device of the present invention enables the surgical team to work more efficiently. For example, normally a surgeon would engage normal laparoscopic devices at the surgical site. The result of that interaction invariably forms debris that obscures the surgeon visualization. To restore visualization the surgeon would normally withdraw these tools and replace them with a laparoscopic suction or hydro dissection tip fixed to a rigid tube. The rigid nature of the distal end of the tube however is often ineffective. The laparoscopic flexible suction/irrigation device of the present invention enables the surgical tools to remain at the surgical site while the laparoscopic flexible suction/irrigation device restores visualization.

The outer flexible cannula 102 of the laparoscopic flexible suction/irrigation device possesses, in one embodiment, inherent curvilinear properties. The outer flexible cannula 102 is elastically deformed upon the insertion of the inner rigid cannula 101 into passageway of the outer flexible cannula 102. Upon the removal 210 of the inner rigid cannula 101 the outer flexible cannula 102 resumes its natural curved shape 220. As depicted in FIG. 2, the inner rigid cannula has been withdrawn 210 to enable the outer flexible cannula 102 to return to a shape consistent with approximately a 45-degree distal end deflection 230. In one embodiment the distal end 160 of the outer flexible cannula 102 can include fiducial markers 240 to aid in its positioning. As the inner rigid cannula 101 is withdrawn 210 further the outer flexible cannula 102 continues to curve. In one embodiment of the present invention the distal end 160 of the outer flexible cannula 102 can achieve a 90-degree deflection with respect to the distal end of the inner rigid cannula. The curved nature of the outer flexible cannula 102 can be achieved by having the distal end 150 of the device tubing elastically pre-bent by a mold, temperature curing or any other manufacturing process to achieve the curving action.

Figure 3:
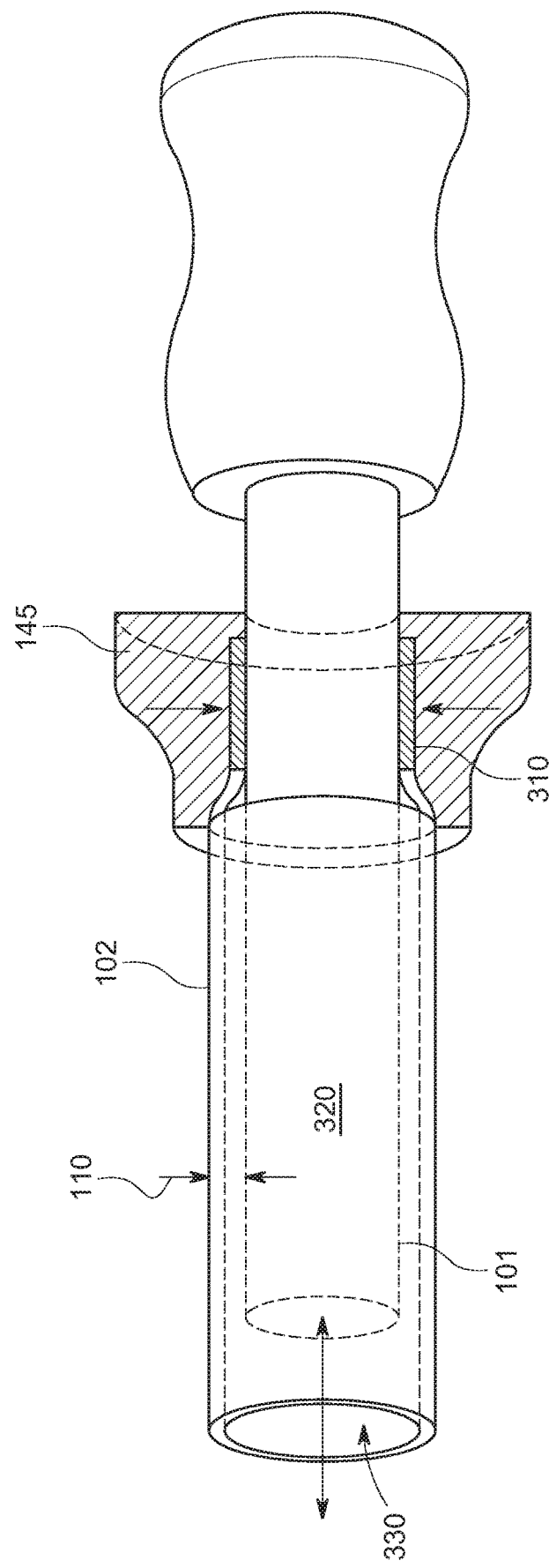
FIG. 3 presents a cut-away view of the laparoscopic flexible suction/irrigation device and its associated clamping device, according to one embodiment of the present invention.

FIG. 3 shows a cutaway side view of the laparoscopic flexible suction/irrigation device of the present invention. The clamping device 145 is fixedly connected to the proximal end 310 of the outer flexible cannula 102. The inner rigid cannula 101, having a first passageway 320 therethrough, is positioned within a second passageway 330 associated with the outer flexible cannula 102. In an open, unclamped, position, the inner rigid cannula 101 is free to translated within the second passageway 330 of the outer flexible cannula 102. A lever coupled to the clamping device constricts the clamping device 145 around the circumference of the outer flexible cannula 102 to form a seal between the inner surface 120 of the outer flexible cannula 102 and the outer surface 130 of the inner rigid cannula 101. With a fluidic seal in place, the application of a fluidic force through the passageway of the inner rigid cannula is conveyed to the distal end of the outer flexible cannula.

Figure 4:
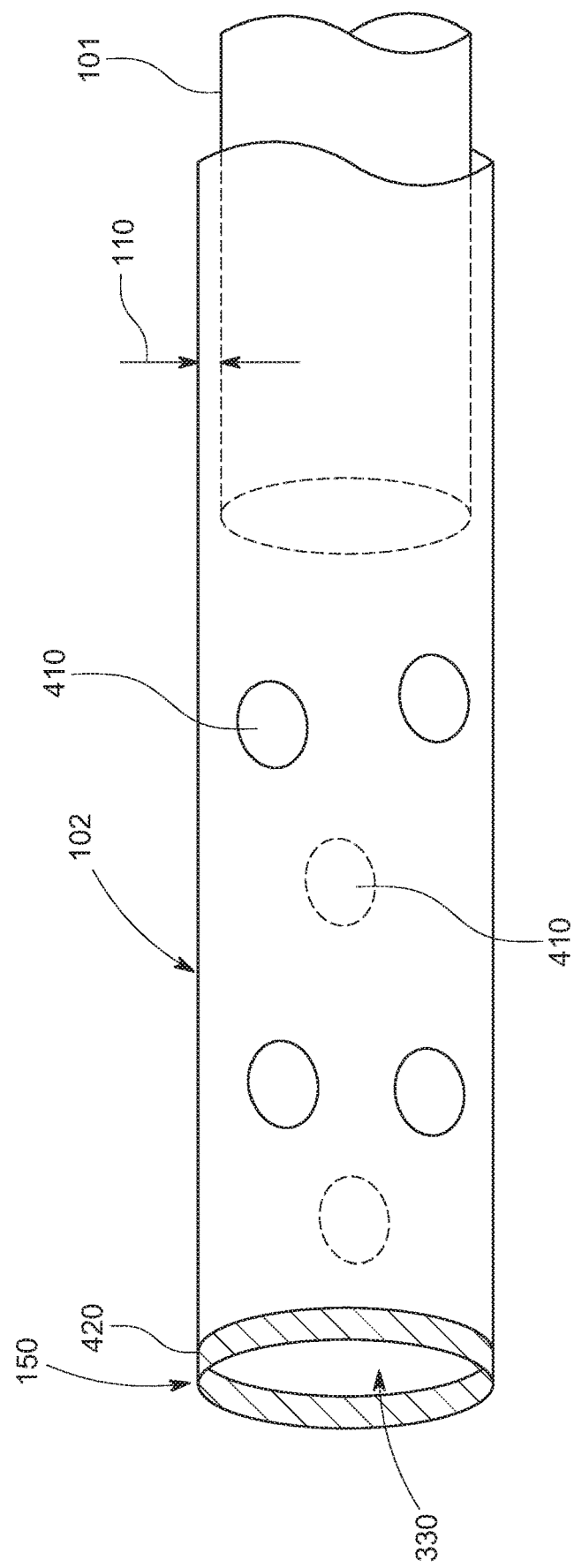
FIG. 4 shows a perspective view of one embodiment of the distal end of the outer flexible cannula with lateral openings by which the laparoscopic flexible suction/irrigation device of the present invention can retrieve fluid.
Figure 5:
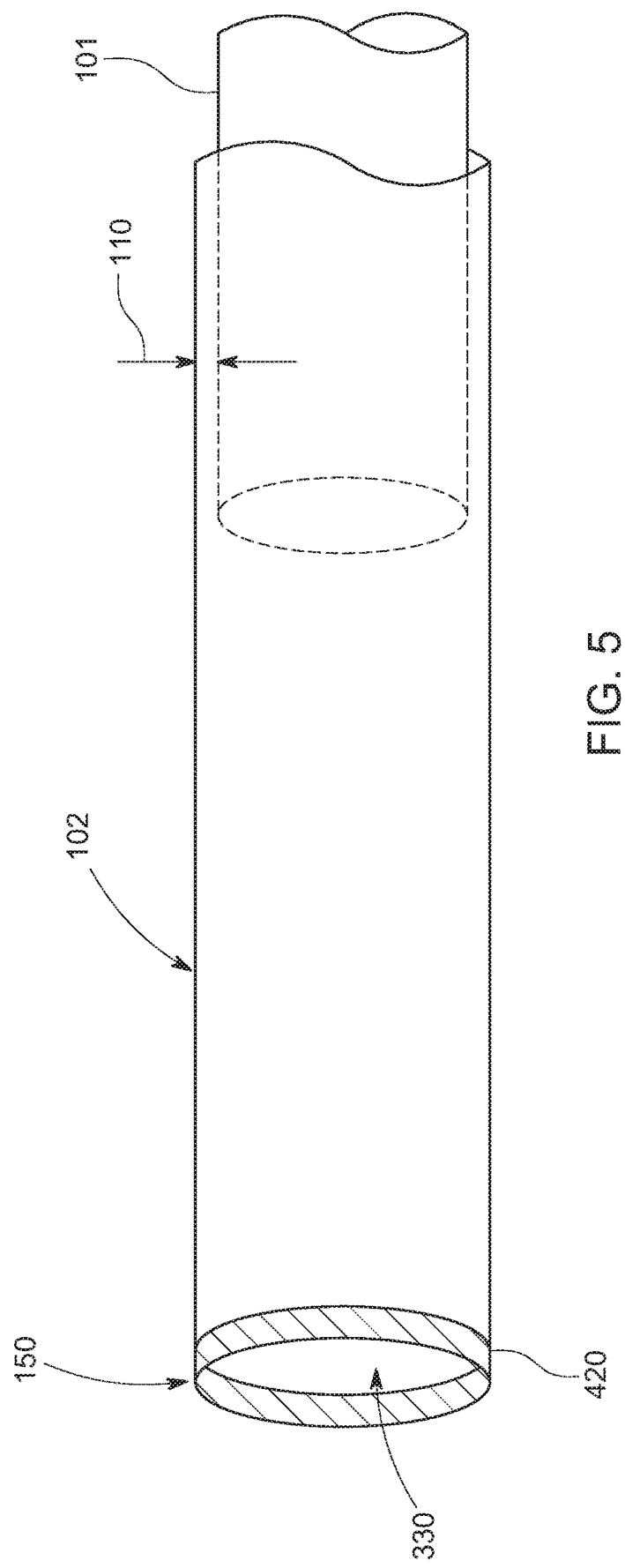
FIG. 5 a perspective view of another embodiment of the outer flexible cannula with a singular opening at the distal end by which the laparoscopic flexible suction/irrigation device of the present invention can retrieve fluid.

The distal end 160 of the outer flexible cannula 102 can have a reinforced passageway 420, top or port holes 410 (shown in FIGS. 4 and 5) to allow for suction release and to disperse fluid when applied to the tip of the inner rigid cannula. The outer flexible cannula 102 of the present invention is, in one embodiment, formed from medical grade tubing. Medical tubing is used for fluid management and drainage as well as with anesthesiology and respiratory equipment, IVs, catheters, peristaltic pumps, and biopharmaceutical laboratory equipment. There are a broad range of materials used to construct medical tubing suitable for use with the present invention. As will be appreciated by one or reasonable skill in the relevant art, the type of material used in the outer flexible cannula determines important performance properties such as abrasion resistance, hardness, flexibility, and durability. The minimum bend radius of the outer flexible cannula is selected such that the outer flexible cannula will not kink or be permanently deformed when extended beyond the distal end of the inner rigid cannula or when positioned over the inner rigid cannula. Moreover, the pressure rating and vacuum rating of the outer flexible cannula is considered in selecting the grade and specification of the material used in its construction. Materials suitable for use in construction of the outer flexible cannula can include Ethylene Propylene (EP), Fluoro-elastomer (FKM), Isobutylene Isoprene Butyl (IIR), Isoprene (IR), Nitrile Rubber (NBR), Polychloroprene (CR), Polyurethane (PU), Silicone Rubber, Styrene-butadiene (SBR) and the like.

Another feature of the outer flexible cannula of the present invention is its insulating characteristics. During laparoscopic surgery the presence of various equipment and surgical devices can result in electrical arcs discharged at the surgical site. If the surgeon is controlling active bleeding or performing dissection with electrocautery, the laparoscopic flexible suction/irrigation device of the present invention can be used to provide better visualization, better outcomes and result in a safer procedure as it can be used actively closer to electrocautery. Indeed, cauterization devices engage such technology to control hemorrhaging at the surgical site. Such electrical discharges, when uncontrolled, can be harmful. Without the device in place, the metallic suction/hydro dissection tips currently in use in the prior art will cause arcing to occur when used close to electrocautery and can cause stray energy to injure a bowel or adjacent structures because of the conductivity of metal. The outer flexible cannula of the present invention insulates the inner rigid cannula substantially reducing or even eliminating any arcing risk.

Figure 6:
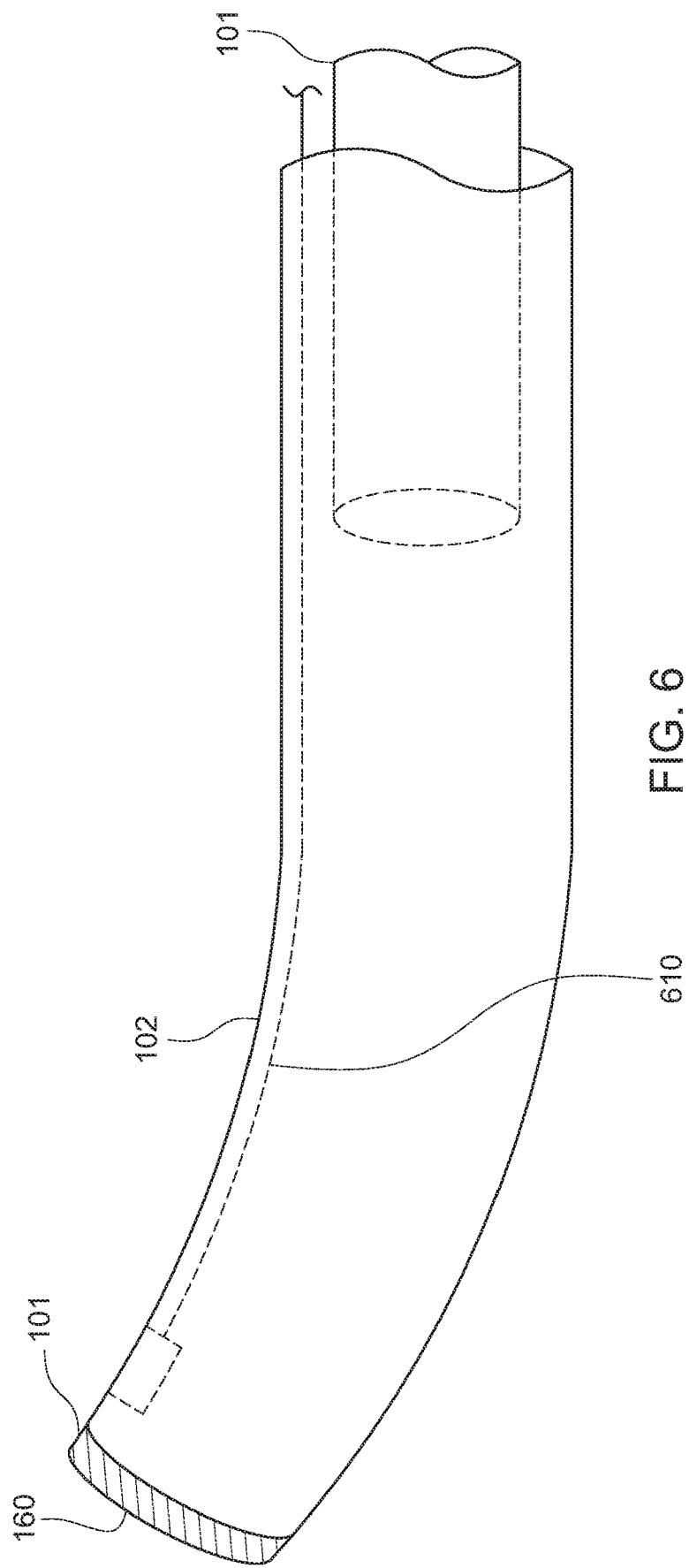
FIG. 6 presents a side view the outer flexible cannula of the laparoscopic flexible suction/irrigation device extended beyond the distal end of the inner rigid cannula whereby the outer flexible cannula exhibits a curvilinear shape.

In another embodiment of the present invention the distal end of the outer flexible cannula can be configured to be curved by one or more cords or cables placed along the passageway of the flexible tubing and along the exterior of the rigid device. In this embodiment of the present invention and as shown in FIG. 6 the cable or cord 610 is actuated at the distal end 160 of the outer flexible cannula 102 after it is extended beyond the suction/hydro dissection tip of the inner rigid cannula. The cord places a sector of the flexible portion of the tube in compression. As one quadrant or sector of the flexible tube is in compression and not supported by the rigid device, the portion of tube extending beyond the rigid device will deflect. In other embodiments multiple cords can be used to control the amount and the direction of the deflection.

The invention can also include magnetic material placed longitudinally along the distal end of the device on one side could be actuated by applying electromagnetic energy causing the tubing to curve as the magnetic material draws closer and causes the side to contract causing the distal end to curve. Other features that enable and control the outer flexible cannula to curve are contemplated and are to be deemed within the scope of the present invention.

Figure 7:
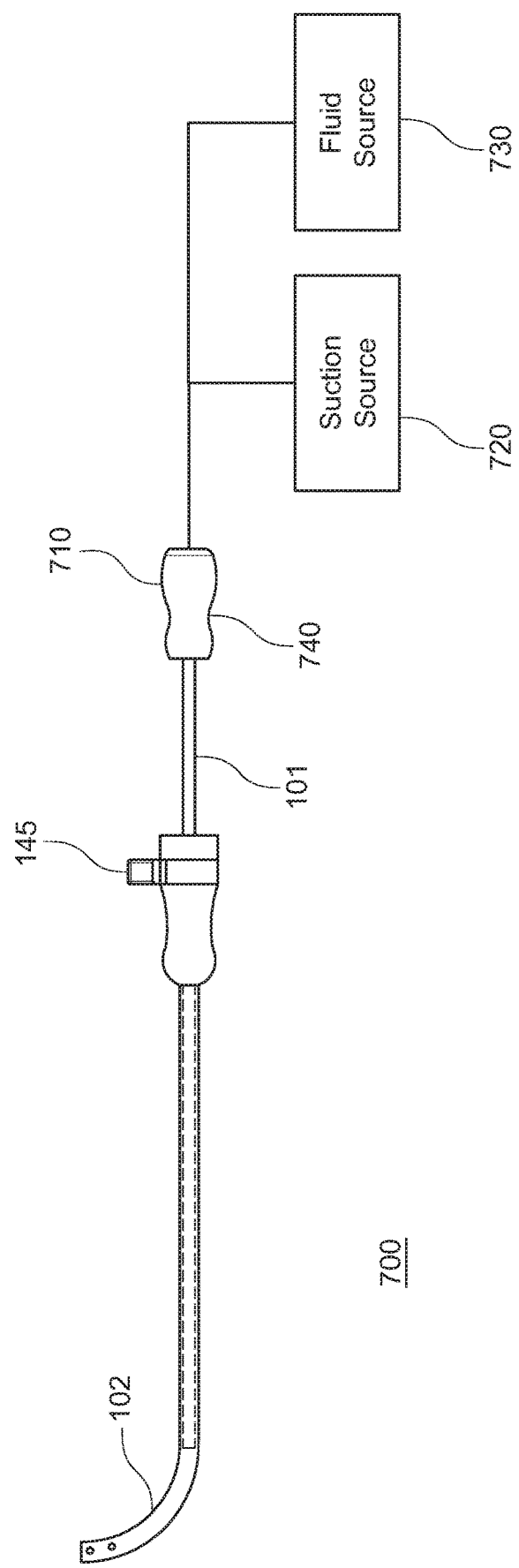
FIG. 7 is a high level view a laparoscopic flexible suction/irrigation system according to one embodiment of the present invention.

FIG. 7 shows a high-level view of a laparoscopic flexible suction/irrigation system 700 according to one embodiment of the present invention. A laparoscopic flexible suction/irrigation device as described herein is inserted into a trocar. The trocar functions as a portal for the subsequent placement of other instruments, such as graspers, scissors, staplers including the laparoscopic flexible suction/irrigation device. Trocars are used a means of introduction for cameras and laparoscopic hand instruments to perform surgery hitherto carried out by making a large incision ("open" surgery). Coupled to the distal end of the inner rigid cannula of the laparoscopic flexible suction/irrigation device is a selectable valve 710. The valve connects a suction 720 or vacuum source and a fluid source 730. As is well known and discussed herein, laparoscopic surgery requires removal of debris and fluid at the surgical site to aid in visualization. Conversely hydro-dissection (using high pressure fluid as a cutting tool) can also be used by the surgeon as an alternative to traditional cutting tools. Other components of the system shown in FIG. 7 can include regulators and hand/foot controls to assist in the utilization of the laparoscopic flexible suction/irrigation device.

Figure 8:
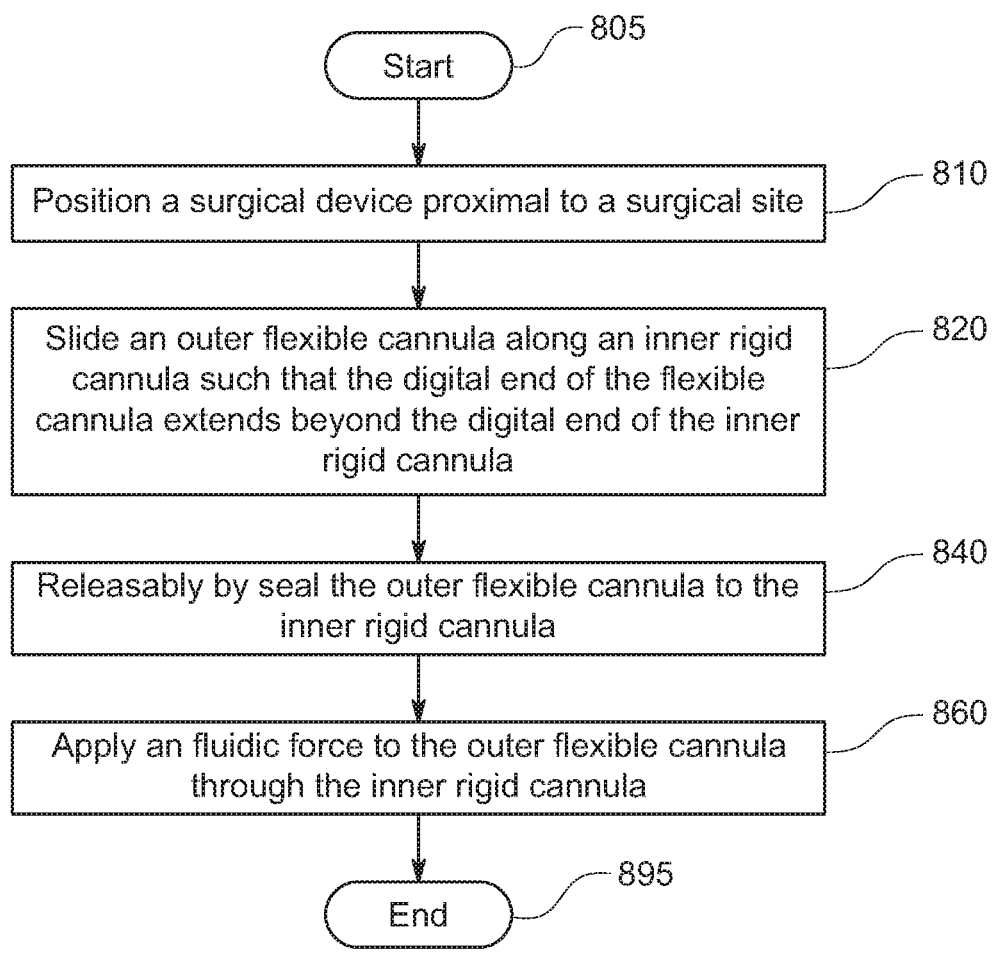
FIG. 8 is a flowchart for one embodiment of a methodology for the laparoscopic flexible suction/irrigation device of the present invention.

FIG. 8 presents a flowchart depicting one methodology for using a flexible suction/irrigation device in laparoscopic surgery consistent with the present invention. In practice, the laparoscopic flexible suction/irrigation device of the present invention is used in conjunction with other laparoscopic tools which are all introduced proximate to the surgical site via a trocar. These implementation methodologies are known within the art and the specifics of their application within the context of the present invention will be readily apparent to one of ordinary skill in the relevant art in light of this specification. Prior to introduction into the trocar the outer flexible cannula is placed over the distal tip of the inner rigid cannula as shown in the prior figures. The device is then fully seated and locked (sealed) onto the tip via the clamping device. At this point the distal end of the inner rigid cannula and the outer flexible cannula are substantially coexistent. The tip of the laparoscopic flexible suction/irrigation device is then inserted through the lumen of a laparoscopic surgical trocar proximal to a surgical site, for example, the abdomen of a patient undergoing laparoscopic surgery. The device is directed by a handle 740 on the proximal end of the laparoscopic flexible suction/irrigation device to a position 810 the distal end inside the patient where suction or irrigation needs to be applied to facilitate the laparoscopic procedure to be performed.

The device of the present invention can, in this configuration, be used in a retracted position "straight" until there is a need to have suction or irrigation applied to an area around a structure or another device being used during the procedure.

According to one embodiment of the present invention, the methodology for use of the laparoscopic flexible suction/irrigation device begins 805 by unlocking the clamping device at the proximal end and retracting the inner rigid cannula. Effectively the retracting of the inner rigid cannula slides 820 the outer flexible cannula along the inner rigid cannula such that the distal end of the flexible cannula extends beyond the distal end (tip) of the inner rigid cannula. At that point the outer flexible cannula is clamped (releasably sealed) 840 to the inner rigid cannula at the proximal end of the inner rigid cannula. The portion of outer flexible cannula, no longer being elastically deformed by the inner rigid cannula and apart from the inner rigid cannula, reverts to is curvilinear shape.

The tip of the outer flexible cannula is thereafter positioned around anatomical structures to areas at the surgical site that would be otherwise unreachable with the straight inflexible configuration to facilitate effective fluid evacuation. Once positioned, a fluidic force (suction) to the outer flexible cannula is applied 860 via the inner rigid cannula. Upon completion of the evacuation, the fluid force is removed and the device can then be unlocked and repositioned ending the process 895. Alternatively, the inner rigid cannula can be extended to once again be coexistent with the outer flexible cannula and thereafter used for straight for rigid dissection, retraction, suction or irrigation. The process can be performed at any time as needed during the procedure to achieve the benefits of function of the curved distal end.

Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The laparoscopic flexible suction/irrigation device and associated methodology of the present invention enables surgeons and their staff to effective remove fluid and debris from recessed, concavities, and hard to reach regions at a surgical site without removing and repositioning other laparoscopic instruments. By simply unclamping and repositioning the relationship between an outer flexible cannula with respect to an inner rigid cannula, the laparoscopic flexible suction/irrigation device introduces a curved cannula through which suction or irrigation can be applied. Upon completion the laparoscopic flexible suction/irrigation device can be reconfigured and yet applied to a different location at the surgical site. The present invention greatly increases visualization of the surgical site and makes the laparoscopic procedure more efficient while reducing risk.

While there have been described above the principles of the present invention in conjunction with a laparoscopic flexible suction/irrigation device and its associated methodology, it is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features that are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features during the prosecution of the present application or of any further application derived therefrom.

The invention claimed is:

1. A surgical device for laparoscopic surgery, comprising:
   an elongated substantially inner rigid cannula having a first passageway extending from a distal end of the inner rigid cannula to a proximal end of the inner rigid cannula;
   a handle connected to the proximal end of the inner rigid cannula;
   an outer, nonconductive, flexible cannula having a second passageway extending therethrough wherein at least a portion of the inner rigid cannula is deposed and translatable within the second passageway of the outer flexible cannula, there being clearance between an interior surface of the outer flexible cannula and an outer surface of the inner rigid cannula to allow fluid flow therebetween, and wherein the outer cannula is disposed within a trocar to a surgical site; and
   a clamping device fixedly connected to a proximal end of the outer flexible cannula and having a mechanism operable to constrict and releasably seal the interior surface of the outer flexible cannula to the outer surface of the inner rigid cannula and wherein the clamping device is operable to establish a predetermined shape of a portion of the outer flexible cannula responsive to securing and forming a seal between the interior surface of the outer flexible cannula to the outer surface of the inner rigid cannula with the portion of the flexible cannula extending beyond the distal end of the inner rigid cannula.

2. The surgical device of claim 1, further comprising a vacuum source coupled to the first passageway of the inner rigid cannula.

3. The surgical device of claim 1, further comprising a fluid source coupled to the first passageway of the inner rigid cannula.

4. The surgical device of claim 1, wherein the outer flexible cannula includes a curvilinear shape memory.

5. The surgical device of claim 1, wherein the outer flexible cannula, having a predetermined curvilinear shape, is elastically deformable so as to accept the inner rigid cannula.

6. The surgical device of claim 1, wherein the clamping device seals the outer flexible cannula to the inner rigid cannula such that a portion of the outer flexible cannula extends beyond the distal end of the inner rigid cannula, causing that portion of the outer flexible cannula to form a predetermined curvilinear shape.

7. The surgical device of claim 1, wherein responsive to the clamping device sealing the outer flexible cannula to the inner rigid cannula at a point where a distal end of outer flexible cannula extends beyond the distal end of the inner rigid cannula, the outer flexible cannula forms a predetermined, preexisting curved shape and wherein a degree of curvature is based on an extent of the portion of outer flexible cannula extending beyond the distal end of the inner rigid cannula.

8. The surgical device of claim 1, wherein the outer flexible cannula translates freely along the inner rigid cannula.

9. The surgical device of claim 1, wherein the inner rigid cannula is substantially coextensive with the outer flexible cannula and wherein the outer flexible cannula is longitudinally and radially movable with respect to the inner rigid cannula.

10. The surgical device of claim 1, wherein the outer flexible cannula is electrically nonconductive.

11. A method of using a surgical device for localized fluid injection or removal during laparoscopic surgery, the method comprising:
    positioning the surgical device proximate to a surgical site through a trocar during surgery wherein the surgical device includes an elongated substantially inner rigid cannula having a first passageway extending from a distal end of the inner rigid cannula to a proximal end of the inner rigid cannula and an outer flexible cannula having a second passageway extending therethrough wherein at least a portion of the inner rigid cannula is deposed and translatable within the second passageway of the outer flexible cannula, there being clearance between an interior surface of the outer flexible cannula and an outer surface of the inner rigid cannula operable to allow fluid flow therebetween;
    sliding an outer flexible cannula along the inner rigid cannula such that a distal end of the outer flexible cannula extends beyond the distal end of the inner rigid cannula;
    releasably sealing the interior surface of the outer flexible cannula to the outer surface of the inner rigid cannula proximate to the proximal end of the inner rigid cannula by a clamping device thereby establishing a predetermined curvature of a portion of the outer flexible cannula based on an extent of the portion of outer flexible cannula that extends beyond the distal end of the inner rigid cannula; and
    applying a fluidic force to the first passageway.

12. The method of using a surgical device according to claim 11, wherein responsive to a portion of the outer flexible cannula extending beyond the distal end of the inner rigid cannula, that portion of the outer flexible cannula forms a select degree of the predetermined curvature directed to a point of interest at the surgical site.

13. The method of using a surgical device according to claim 12, further comprising directing the distal end of the outer flexible cannula to point of interest at the surgical site by restoring the portion of the outer flexible cannula extending beyond the distal end of the inner rigid cannula to a select degree of the predetermined curvature.

14. The method of using a surgical device according to claim 11, further comprising positioning the inner rigid cannula substantially coextensive with the outer flexible cannula, wherein the outer flexible cannula is longitudinally and radially movable with respect to the inner rigid cannula.

15. The method of using a surgical device according to claim 11, further comprising elastically deforming the outer flexible cannula so as to conform to the inner rigid cannula.

16. The method of using a surgical device according to claim 11, further comprising translating the outer flexible cannula freely along the inner rigid cannula.

17. The method of using a surgical device according to claim 11, wherein the fluidic force removes fluid from the surgical site.

18. The method of using a surgical device according to claim 11, wherein the fluidic force injects fluid to the surgical site.

* * * * *